US005139025A

United States Patent [19]

Lewis et al.

[11] Patent Number: 5,139,025

[45] Date of Patent: Aug. 18, 1992

[54] METHOD AND APPARATUS FOR IN VIVO OPTICAL SPECTROSCOPIC EXAMINATION

[75] Inventors: Gary D. Lewis, St. Clair Shores, Mich.; Hugh F. Stoddart, Groton, Mass.

[73] Assignee: Somanetics Corporation, Troy, Mich.

[21] Appl. No.: 329,945

[22] Filed: Mar. 29, 1989

Related U.S. Application Data

[63] Continuation-in-part of Ser. No. 542,022, Oct. 14, 1983, Pat. No. 4,570,638.

[51] Int. Cl.$^5$ ................................................ A61B 5/00
[52] U.S. Cl. ..................................... 128/665; 128/664
[58] Field of Search ............... 128/632, 633, 653, 665, 128/664, 666; 250/358.1, 339; 356/432

[56] References Cited

U.S. PATENT DOCUMENTS

| | | | |
|---|---|---|---|
| Re. 31,815 | 1/1985 | Alfano | 128/665 |
| 4,013,067 | 3/1977 | Kresse et al. | 128/666 |
| 4,223,680 | 9/1980 | Jöbsis | 128/633 |
| 4,321,930 | 4/1982 | Jöbsis et al. | 128/633 |
| 4,515,165 | 5/1985 | Carroll | 128/664 |
| 4,570,638 | 2/1986 | Stoddart et al. | 128/665 |
| 4,649,275 | 3/1987 | Nelson | 128/358.1 |
| 4,655,225 | 4/1987 | Dahne et al. | 128/664 |

OTHER PUBLICATIONS

IBM Technical Disclosure Bulletin, vol. 10 No. 3, Aug. 1967 "Stacker Selection System" by A. K. Brooks & C. J. Kellerman, pp. 225–226.
IBM Technical Disclosure Bulletin, vol. 10, No. 3, Aug. 1967 "MICR Automatic Gain Control" by R. W. Arnold, pp. 227–228.
The Waters Company Advertisement, received in PTO Oct. 7, 1965 on X-350 Oximeter (Rochester, Minn.).

Primary Examiner—Stephen C. Pellegrino
Assistant Examiner—Steven J. Shumaker
Attorney, Agent, or Firm—Price, Heneveld, Cooper, DeWitt & Litton

[57] ABSTRACT

Methodology and apparatus for the clinical evaluation of biological matter, in particular human anatomy, examined in situ and in vivo, by selective spectral light transmissivity. An optical probe introduces selected light spectra into the examination subject at a first position and resulting light intensity at a second position located some distance from the infusion point is measured; also, light reception preferably occurs at at least one other location, and the effective distances between these locations and the infusion point are determined. The light energy received at the distant points is quantified and conditioned by use of the effective distances from the infusion point and/or from one another, and also by contrasting the data from the two differently-located reception points, such that the resulting data quantitatively characterizes intrinsic internal tissue characteristics in an absolute sense, devoid of particular individual characteristics and variations such as skin pigmentation, boundary composition or state, etc. The methodology is especially characterized by the selection and use of particularly-located first and second light-reception positions whose locations with respect to the point at which the light spectra are introduced define particular zones of interrogation and analysis, and whose location with respect to one another may be comparatively examined (e.g., differenced) to selectively define a particular internal volume whose structure or conditional state is to be examined, quantified, and/or analyzed, all of which is accomplished on a non-intrusive in vivo basis.

23 Claims, 4 Drawing Sheets

METHOD AND APPARATUS FOR IN VIVO OPTICAL SPECTROSCOPIC EXAMINATION

CROSS REFERENCE TO RELATED APPLICATIONS

This application is a continuation-in-part of prior application Ser. No. 542,022, filed Oct. 14, 1983 (now U.S. Pat. No. 4,570,638) and is also related to prior U.S. Pat. applications Ser. Nos. 827,526 and 830,578 (now U.S. Pat. No. 4,817,623), the disclosures of which are incorporated herein by reference as fully as though set out in total.

TECHNICAL FIELD

This invention relates generally to optical spectrophotometric examination and/or analysis of tissue and/or other biological materials or substances, especially human tissue or other such biological substance, i.e., use of spectrally-selective optical (light) propagation and response technology for such examination and/or analysis purposes; more particularly, the invention relates to methodology and apparatus involving the use of optical spectrophotometric technology on an in vivo basis in human subjects for analytic and diagnostic purposes. Still more particularly, and in some of its more specific attributes, the invention relates to certain novel applications and methodology in examination of, and the production and presentation of clinical physiological data with respect to, human anatomy by use of optical response observations, e.g., light transmissivity response measurements and characterization; in particular involving the use and relative positioning of two or more receivers for the light spectra introduced into the examination subject and detected after undergoing reflection, scatter and absorption effects within the subject, by which a particular internal volume may be selectively examined spectrophotometrically.

BACKGROUND OF THE INVENTION

In academia, and particularly in biological and medical research activities, among practically innumerable studies, experiments and laboratory examinations, a relatively small but frequently recurring interest has been shown in the use of light, in various different forms, as an investigative and/or diagnostic tool or instrumentality. A relatively primitive emanation of this interest is evidenced in the various forms of transillumination which have been experimented with and used in many different ways over a great many years, probably dating back into antiquity, and in general utilizing light relatively crudely, i.e., as a visual aid, to help produce visually-perceptible shadows, shapes and images within or upon what would otherwise be substantially opaque objects or surfaces. In other more complex procedures, light energy of particularly-selected parameters is impinged upon or injected into the subject matter to be investigated and interpreted from the standpoint of the quantity or nature of the light detectable at another location, typically opposite the point of injection. This approach frequently includes the use of spectrometers at the point of detection, and may or may not involve the use of particularly-selected wavelengths of light for application to the subject under study.

Thus, in earlier efforts utilizing basic transillumination, a typical approach would be to utilize a source of visible light coupled by a tubular shield or the like to a translucent body portion or object which is then viewed carefully from the opposite side with the human eye, often aided by various reflectors, magnifiers and the like. One immediately-available example of such a procedure is that utilized by physicians for examination of human sinus conditions. An example of the more complex type of procedure would be a scientific study such as for example is illustrated in scholarly publications of the type entitled "Infrared Microspectrum of Living Muscle Cells," by Darwin L. Wood (Science, Vol. 1, Jul. 13, 1951), in which different particular individual types of muscle fibers were placed between transparent plates and placed in the radiation beam of a microspectrometer, where they were subjected to various wavelengths of light up to about ten microns, with the detected transmission intensities being plotted according to wavelength. With respect to the efforts to use transillumination generally, further reference is made to publications such as that by M. Cutler, M.D., in the Jun., 1929, issue of *Surgery, Gynecology and Obstetrics*, entitled "Transillumination As An Aid In The Diagnosis Of Breast Lesions," and as to the more complex spectrophotometric procedures, reference is made to an article in the Aug. 5, 1949, issue of Science (Vol. 110), by Blout and Mellors, entitled "Infrared Spectra Of Tissues."

While the aforementioned article by Cutler discussed basic transillumination procedures for diagnosis of breast disease as early as 1929, a number of proposals for refinement and enhancement of the basic transillumination procedures have been suggested in intervening years. Thus, the use of color film was proposed in 1972 by Gros and Hummel, and Ohlsson et al. proposed in 1980 the use of infrared film rather than ordinary color film, both using visible yellow light as well as infrared or rear infrared light as the illumination. Carlson has further proposed the use of a Vidicon system as a detector or collector, but the ultimate analysis and interpretation is nonetheless done visibly.

In the area of spectrophotometric analytic and diagnosis efforts, infrared oximeters have been developed and utilized in relatively recent years for non-invasive monitoring of the oxygenation of blood in humans and other specimens, most typically by contact with the ear or finger extremity, a selected infrared wavelength being coupled to the involved body portion with detection occurring on the opposite side of such portion, variations in the light energy detected being directly indicative, after appropriate calibration, of the oxygen content of the blood flowing through the affected body portion, as a result of the known absorption references of particular infrared wavelengths by oxygenated hemoglobin. Somewhat analogous observations and/or phenomena may be discerned by contemplation of publications such as those by Blout and Mellors, noted above, which noted a dramatic increase in the intensity of light as the 9.3 micron band in cancerous breast tissue as compared to normal breast tissue and the proposed explanation that the 9.3 micron band is also one of the strong intensity bands for the enzyme ribonucleaes, which rapidly increases in amount in rapidly proliferating cancer cells.

Various publications of Frans Jobsis commencing in about 1977 and including U.S. Pat. Nos. 4,223,680, 4,281,645, 4,321,930 and 4,380,240 are based upon a somewhat analogous although specifically different reported phenomena, i.e., the spectrally distinctive absorption characteristics associated with the cellular enzyme cytachrome a, $a_3$, which in turn is said to be integrally associated with, and indicative of, oxydative metabolism. On this basis, Jobsis proposed the use of a particularly-selected measuring wavelength and another carefully selected reference wavelength to produce apparent differences in detection level, which differences were said to demonstrate, and actually be indicative of, organ vitality or viability, since indicative of oxydative metabolism and therefore of oxygen sufficiency, the premise being that the chain of causation between the observed measurements and the body organ believed to be under investigation, i.e., internally subjected to the injected light, was complete and inclusive.

GENERALIZED DESCRIPTION OF THE INVENTION

In a broad and underlying sense, the present invention rests upon a basic foundation of optical spectrophotometry as used in connection with physiologic conditions and principles as generally described in the above-referenced related applications, involving the effects of light transmissivity (scatter and absorption) within the tissue under observation. That is, from one standpoint, the invention is broadly based upon the principle that light, and especially selected wavelengths of light (generally within the band of from 0.6 micron to 1.5 micron, by way of example) are transmissible through at least portions of the human body in varying degrees as a significant and characteristic function of particularizing scatter and absorption effects of the specific tissue under examination.

Thus, it has been found in accordance with one aspect of the invention that a given body portion will, when suffused with a selected group of wavelengths, exhibit a definitive and repeatable optical response, which may be used to characterize and demonstrate a particular physiological condition and composition and, it is believed, to show abnormality or anomaly, particularly when compared to other such responses taken from the same individual (i.e., person) both at other points in time and/or from other and complementary or analogous body portions (e.g., the opposite breast), as well as when compared to readings or profiles, and/or composites thereof, taken from the same body portions of other humans, especially related groupings of particular humans.

Further, the invention provides methodology and apparatus for obtaining optical response data indicative of intrinsic tissue characteristics and independent of individual and ethnic factors such as color, degree of pigmentation, age, skin thickness, etc., which is uniquely useful in the above-noted type of approach, as well as in other and more general clinical ways.

More particularly, the invention provides methods and apparatus for obtaining spectral transmissibility data for clinical study and analysis, particularly of human anatomy viewed in vivo, to provide a further clinical instrumentality for the study of such anatomy, hopefully to help bring about better understanding of its physiology, particularly with respect to its current status, and also with respect to effects caused by anomaly, abnormality, disease, injury, trauma and/or other adverse conditions and states.

In a broad sense, the invention is directed to a new method and apparatus for obtaining optical response data by examining biological tissue in vivo, yielding highly useful information as to the intrinsic composition, condition and physiology of an internal volume of tissue whose location and size depends upon the relative positioning and location of optical probes.

In a more particular sense, the invention contemplates the injection of light (and particularly sequential bursts of particularly-selected light wavelengths, or narrow bands) into the selected body part at a given location, and the detection of the amount of resulting light which emerges and is detected, or received, at least two locations, one typically disposed nearer the point of injection and one or more others, typically located relatively farther from the injection point.

Generally speaking, the two such detection locations are chosen to satisfy two conditions; i.e., the injected light must have similarly passed into and out of the skin at each different location, and the light must have sampled (propagated through) at least partially different areas and amounts of internal tissue. By comparative analysis of the resulting light reception data, effects related to impingement and entry (as well as exiting) of the light through the skin and a given adjacent area are cancelled out, and the resulting data thus pertains to and in effect samples the tissue within a specifically selected internal volume or region. Since the relative geometrical locations and spacing of the light receivers are known and the nominal optical distance, and particularly the difference between the optical distance between the location of the near receptor, or receiver, and that of the far receptor or receiver, is determined in accordance with the invention, these are used as conditioning factors in quantifying the resulting light-reception data. Thus, such data is directly and meaningfully appropriate for use in comparative studies of, and for averaging and compositing with respect to, different individuals regardless of whether they are of the same or different racial, ethnic or pigmentation characteristics, and regardless of particular physical differences and the like, from one subject to another.

Accordingly, the present invention provides methodology and apparatus which are especially characterized by the selection and use of particularly-located first and second light-reception positions whose locations with respect to the point at which the light spectra are introduced define particular zones of interrogation and analysis, and whose location with respect to one another may be comparatively examined (e.g., differenced) to selectively define a particular internal volume whose structure or conditional state is to be examined, quantified, and/or analyzed, all of which is accomplished on a non-intrusive in vivo basis.

DETAILED DESCRIPTION OF THE PREFERRED EMBODIMENT

Figure 1:
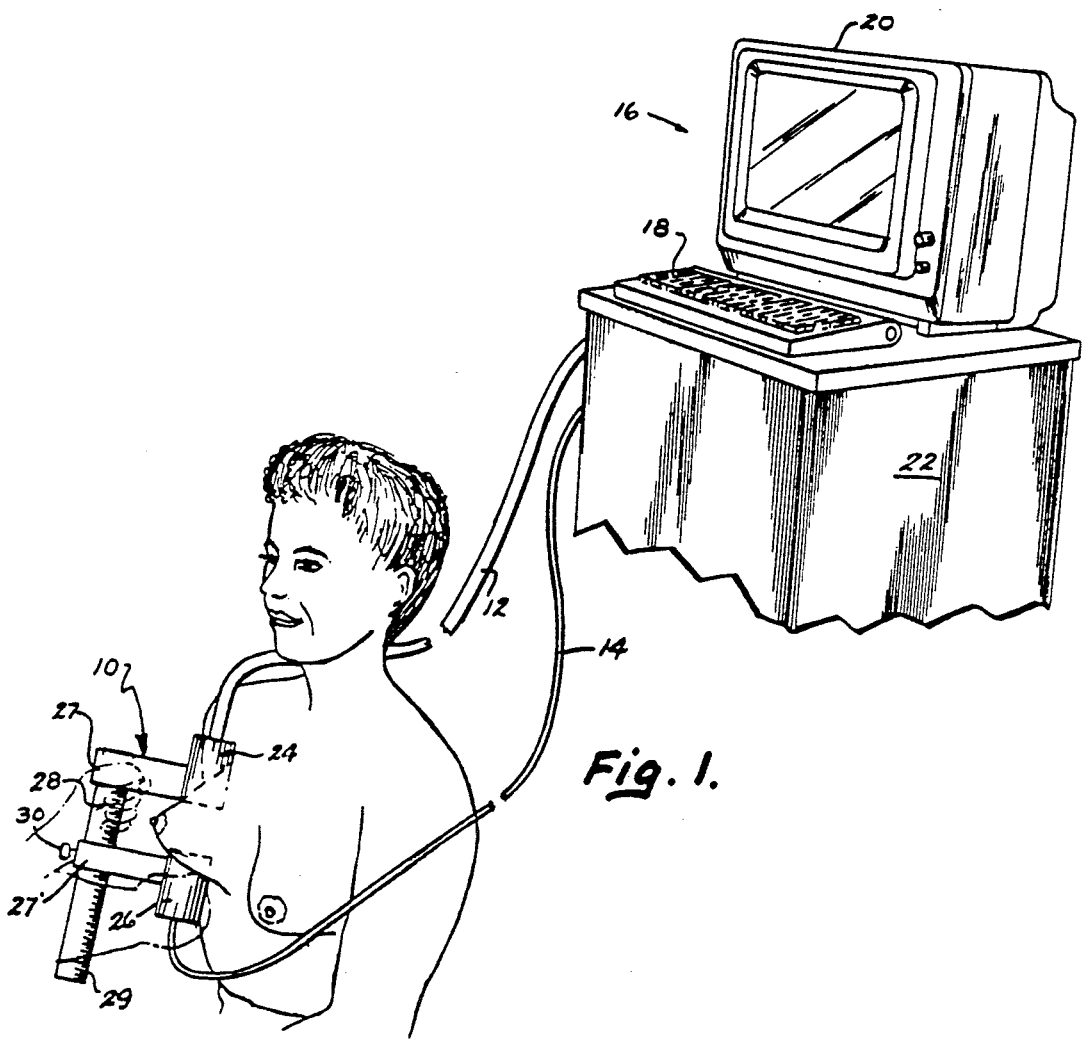
FIG. 1 is a pictorial illustration showing an overall system in accordance with previous and incorporated U.S. Pat. No. 4,570,638, which also illustrates the general environment and apparatus in accordance with the present invention.

The general nature and general usage of one form of apparatus in accordance with the invention is illustrated pictorially in FIG. 1, which is reproduced from Applicants' earlier U.S. Pat. No. 4,570,638, incorporated herein by reference. Stated in the most basic terms, optical measurements or readings are taken by use of a manually-manipulatable test instrument 10 which is coupled by cables 12 and 14 to a control unit 16 which includes an input keyboard 18 for actuation and control purposes, a CRT visual display 20 on which data may be displayed in various formats, and a housing 22 in the form of a cabinet which encloses associated light sources, electrical supply apparatus, data-handling electronics and data-processing apparatus including for example a microcomputer (which may be a small digital device of the type known as a "personal computer," e.g., the IBM "P.C." or generally similar device), together with interconnected data storage (e.g., floppy disk drive) and a digital printer or plotter of a conventional nature.

With continuing reference to the apparatus shown in FIG. 1, it will be observed that the test instrument 10 includes a first side or portion 24, referred to hereinafter as a "component member," as well as a second such portion or "component member" 26, both of which are, in this particular embodiment, disposed in mutually-aligned opposition. This mutual alignment (geometry), selected for this particular application, is maintained by support means comprising, in this example, fixed and movable carriers 27, 27′, respectively, mounted upon a rigid interconnecting alignment and positioning bar 28 which carries length-measurement indicia 29.

Figure 2:
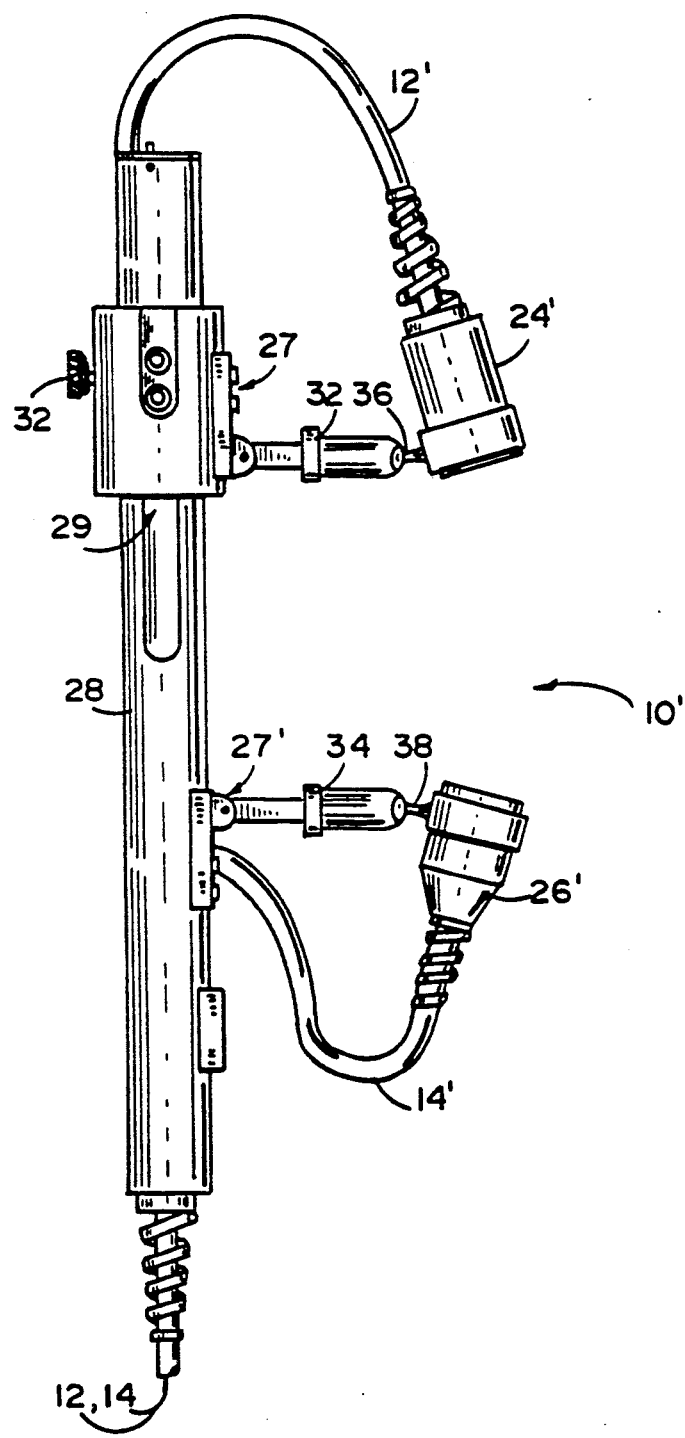
FIG. 2 is an enlarged, side elevational view of an optical probe generally in accordance with Applicants' co-pending and incorporated application Ser. No. 827,526, which further illustrates apparatus useful in understanding the present invention.

While many different particular structures or mechanisms may be utilized for the basic purpose of maintaining a given desired geometric relationship, i.e., "alignment," of the "component members" while permitting desired relative movement, one relative basic arrangement for axial relationships of the type illustrated in FIG. 1 is that of a modified dial caliper. A more refined version of such a device is shown in FIG. 2 and fully described in Applicants' related and co-pending application Ser. No. 827,526, filed Feb. 10, 1986, which is also incorporated by reference herein.

The significance of the nominal optical distance information readable from the indicia on the bar 28 or otherwise provided by the test instrument 10 will be explained more fully hereinafter, but it should be noted that the availability and utilization of such information is decidedly important to the invention. Thus, whatever spacial relationship or geometry is desired for the light source and receivers in a given embodiment, the support means utilized must be arranged to provide the effective or nominal optical distances involved, whether the component members are fixed or movable. In the embodiment illustrated in FIG. 1, this information is entered into the computer via the keyboard 18 by the operator, but it may be preferred to utilize a form of the test instrument 10′ such as that shown in FIG. 2 and described in co-pending application Ser. No. 827,526, having a transducer which automatically provides this information as a coordinated part of the overall procedure.

As may further be seen in FIG. 1, the test instrument 10 utilized for that procedure places the two component members 24 and 26 on opposite sides of the breast or other such body extremity which is to be examined. In the case of the human female breast, several different readings are preferably taken, for purposes discussed more fully in the referenced and incorporated related cases, and in that procedure the orientation of the test instrument, and of the two component members, is preferably generally vertical in taking each such measurement or reading. This results from the particular interstructure of the breast, however, which is much more symmetrical from one vertical section to the next. Thus, in the breast-examination procedure of the referenced co-pending cases, the instrument is moved from place-to-place by manual manipulation, and in each instance the two component members are moved apart to the extent necessary, placed over the breast in the desired positioning, and then gently moved toward one another to the extent necessary to provide full contact between the inner surface of each component member and the breast, so as to preclude the entry or exit of any light from between the breast and each of the component members.

The structural nature of component member 24 is disclosed in detail in related and referenced U.S. Pat. No. 4,570,638 and a more refined and improved version thereof is disclosed in co-pending application Ser. No. 827,526. Generally speaking, this member includes a cylindrical outer shell or cover, which may be a thin metal or polymeric member, and houses an optical emitter (e.g., a fiber optic terminal coupled to a source of selected light spectra) and one or more optical detectors. The detectors may be a light guide fitted to a fiber optic cable which exits the component member with the light source fiber optic, collectively constituting the aforementioned cable 12. In the embodiment illustrated in FIG. 1 and described in detail in Applicants' prior U.S. Pat. No. 4,570,638, the detectors in component member 24 are disposed along a circular arc which is centered upon the optical fiber constituting the light-emitting source, and the distance (radius) between such optical fiber cable and the receivers should, in that embodiment, preferably be in the range of about one to three centimeters, preferably not more than about two centimeters. As will be seen below, this distance is an important factor, and is selected to accomplish particular purposes, since the detector associated with member 24 constitutes a "near" receiver which receives light energy which has been introduced ("injected") by the optical fiber bundle into the particular body portion or extremity with respect to which clinical data is desired to be obtained, but which has traversed a shorter path, having entered that body portion and merely encountered reflection and "backscatter" from the internal tissue located directly beneath the skin rather than deep within the subject.

Thus, the light energy detected by the "near" detectors has passed through the skin of the subject and through the adjacent internal tissue of the breast (or other body portion) but has immediately exited by passing back outward through the skin, at a point relatively near the source. This "near" detection signal is very important in accordance with the invention, as will be explained more fully hereinafter, and should not include light which has merely passed directly from the end of the fiber optic into the detectors without ever having passed into and out of the skin and adjacent tissue of the subject. In the particular embodiment illustrated in prior Pat. No. 4,570,638, the light energy detected at the "near" position represents light reflected generally toward the source, which has not traversed substantial distances within the breast tissue and emerged far away from the source; however, in accordance with the broader aspects of the disclosure in this prior patent, and with the more particular discussion set forth hereinafter, the "near" receivers may be selectively positioned so that the apparatus "samples" a particular area or zone in the test subject constituting a selected tissue volume or location.

The "far" receiver component 26 for the embodiment of prior Pat. No. 4,570,638, illustrated in FIG. 1, is similar in basic structure to component 24 discussed above, including an outer shell through which an electrical cable 14 enters and exits. Component 26 does not include a light source, however, and instead houses a desired array of light detectors (i.e., one or more detectors), mounted in a predetermined location. As noted in prior Pat. No. 4,570,638, and as described fully below, the "far" receiver may be located much closer to the source and "near" receiver than is the case in the apparatus shown in FIG. 1 since the particular location selected for the far receiver is coordinated with that selected for the "near" receiver, such that the apparatus "samples" a particular area or zone in the test subject constituting a selected tissue volume or location.

It should be understood that terms used herein such as "direct" or "transmitted" and "reflected" are adopted primarily for purposes of convenience and illustration, and not to indicate that there are fundamental differences between the light energy that emerges at any given point from the selected body portion after injection. Actually, it is believed that all injected light undergoes multiple and diverse scatter effects throughout its tortuous path of propagation within the body portion in which it has been injected. Thus, the present invention contemplates use of the overall optical response provided by comparative analysis of the "near" and "far" detection signals, which response is viewed as complex in nature and quite conceivably involving molecular (Rayleigh) scattering, particle (Mie) scattering, index (Fresnel and Christiansen Effect) scattering, fluorescence (especially infrared fluorescence), inelastic (Raman) scattering, and both spectral and non-spectral energy absorption. Thus, the circumstances and the methodology are considerably more complex than simple in vitro laboratory spectrophotometry, and the responses obtained in accordance herewith may well depend upon such factors as molecular structure, the types and size distributors of the cells, the amount, nature and distribution of fat cells, and of connective tissue, the blood supply and vascularization metabolism, the lymph system, and glandular activity.

As indicated previously in conjunction with the discussion of FIG. 1, the component members 24 and 26 are, in that particular embodiment, held in direct alignment with one another by the carriers 27, 27' and the bar 28. More particularly, in this arrangement the alignment is such that the light-injecting fiber optic or other such source component is substantially aligned along the same axis with at least one of the "far" detectors. This arrangement is not at all necessarily utilized, however, as pointed out more fully below.

To a substantial degree, a primary aim of the present invention is to obtain clinical, physiological data for selected body portions, and particularly of selected tissue location, by optical response methodology. More particularly, the clinical data obtained in accordance with the present invention represents intrinsic, internal tissue properties particular to a selected location within the test subject.

In accomplishing the objectives of the invention, the above-noted means for determining the particular distance between the component members of the optical probe (i.e., the "nominal optical distance") involved in a given measurement or scan is of considerable importance, as is the determination and appropriate usage of both "far" light propagation data and "near" data. With respect to the second such point, a significant feature of the present invention is the realization that "near" transmissibility data should be obtained and in effect used as a measure of the light energy actually injected into the interior of the body portion under examination, after the effects of impingement upon and passage through the skin and immediately adjacent tissue, etc. This "near" detection level is subtracted from the "far" detection data, since by so doing one may compare the amount of light energy which has passed completely through, or at least traversed a substantial portion of, the body portion under examination with the amount of light energy which has only transmissed a lesser volume of internal tissue, and thus remove from consideration the many data-modifying characteristics arising from individual differences of skin, bone, etc., as well as all such characteristics representative of a tissue volume adjacent to the particular volume desired to be selectively examined.

Furthermore, the knowledge and appropriate utilization of the particular nominal optical distance involved in each different optical scan over whatever different wavelength spectra have been selected and over whatever different body portion or path has been selected is also of great significance, since this optical distance is utilized in accordance with the invention to condition the data obtained and thus remove the otherwise inherent variation of light energy propagation as a function of optical distance or thickness. In this connection, it should be clearly understood that the particular arrangement illustrated in FIG. 1, with axial alignment of the receivers and close positioning of the "near" detector to the light source, is not at all the only effective such arrangement. That is, while at least one "near" and one "far" detector are required, they need not be positioned on a straight-line basis if some other (e.g., relative angular positioning with respect to the light source) arrangement is desired, as for example to better accommodate a particular anatomical area to be studied. In any such arrangement, the effective or nominal optical paths involved for the particular positions of the receivers must be determined, since such distances characterize the different tissue volumes sampled by the different receivers. That is, proximity of the near detector to the point of light injection may be "built into" the scale which is read to determine the optical distance for the "far" detector, and where both locations are fixed the corresponding distances will of course be predetermined and may be used directly, without measuring or reading out. In any case, utilization of the measured or otherwise-determined effective or resultant optical distance, by which the mean optical path length may be determined or closely approximated, is accomplished y using it as the "thickness" or length parameter in application of the exponential relationship attributed to Beers and known as Beers' Law, to develop intrinsic light propagation magnitude values for the internal tissue of the selected body portion.

While it is not the purpose of this disclosure to focus upon any particular methodology and/or apparatus for actually making this data compensation or specifically implementing the data-conditioning principles, it may be noted that data-handling procedures of this general nature are readily and indeed routinely obtained through use of known techniques and routines in the use of digital computers, and that appropriate results may also be obtained directly through electrical signal-processing approaches, in hardware (circuitry), since discrete digital components such as adders, subtracters and digital dividers are of course in widespread use and widely diverse availability. It is the general underlying principle and methodology of such approaches which is here involved, i.e., arrival at intrinsic-type data by conditioning the signal values actually received from the "far" receivers through use of the "near" receiver data, together with use of the nominal optical distance measurement determined for each particular measurement set, as discussed below.

As indicated previously above, the particular location selected for the "near" and "far" receivers or detectors symbolized by first component member 24 and second component member 26 in FIG. 1 (and by the comparable members 24', 24" and 26', 26" of FIGS. 2, 3 and 4) provides the capability of selecting a particular volumetric sample within the test subject whose characteristics may be non-invasively examined and quantitatively determined in accordance with the present invention. Thus, where the "near" and "far" receivers are positioned in the manner illustrated in FIG. 1, the tissue volume which is examined is somewhat like that pictorially illustrated in FIG. 5, wherein a hypothetical in vivo body extremity or portion 30 (e.g., the human breast, generally in accordance with Applicants' prior Pat. No. 4,570,638, or other such body extremity capable of being transmitted by selected light spectra) is illustrated with the light source portion 24a (providing a source "S" of selected light spectra) located at the twelve o'clock position, the "near" receiver 24b located at approximately the one o'clock position, and the "far" receiver 26a located at the six o'clock position. In this arrangement, essentially the entire internal volume of the test subject 30 is sampled by subtracting the output $O_1$ received at the near receiver 24b from the output $O_2$ received at the far receiver position.

As noted in prior Pat. No. 4,570,638, however, the near and far receivers do not have to be disposed in the particular locations, or at the relative spacing, depicted in FIGS. 1 and 5, and may be positioned in other locations so that other and different particular tissue volumes will be examined, in a selective manner. Thus, the optical probes illustrated in FIGS. 2 and 3 show other dispositions of near and far receivers, which may be used for this purpose in accordance with the "near-far" subtractive processing methodology noted above and described mathematically herebelow.

The optical probe 10' shown in FIG. 2 is much like that described in detail in Applicants' co-pending application Ser. No. 827,526; however, whereas that particular application shows an optical probe whose two component members have relatively fixed or "hard-mounted" positions, the component members 24' and 26' in the probe 10' shown in FIG. 2 include means for changing the relative orientation and positioning of the "near" and "far" 1. receivers, e.g., a manually-operable telescoping slide joint 32, 34 by which the two such component members may be moved further inboard or outboard from the main support portion of the probe. Furthermore, the probe 10' of FIG. 2 includes rotatable couplings 36, 38 for the component members 24' and 26', respectively, by which such members may be rotated with respect to one another and with respect to their corresponding support members. Both such position-changable mechanisms should permit easy position adjustments by hand, and preferably are position-retaining, or at least lockable in selected positions by threaded collars or thumbscrews. Both such mechanisms may be generally of a conventional nature and utilize known mechanisms such as friction-lock slide members, spring-loaded ratchet-type or other such detents, etc.

Figure 5:
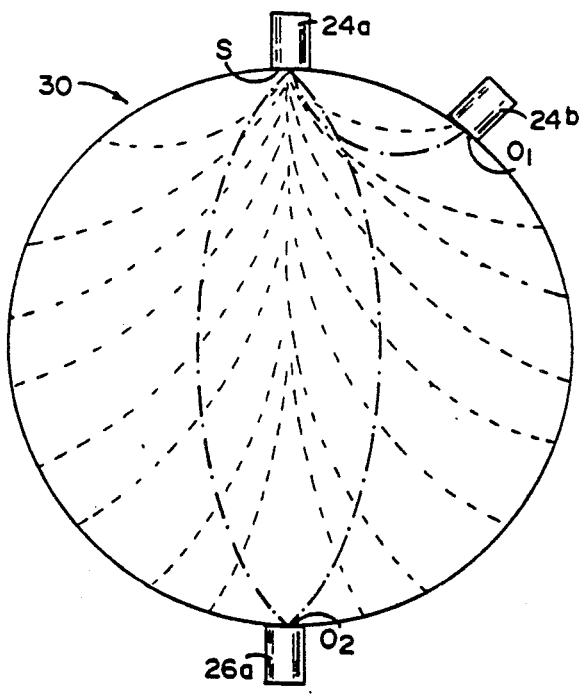
FIG. 5 is a pictorial, schematic illustration showing a first arrangement of light source and light-detection receivers helpful in understanding the present invention.
Figure 6:
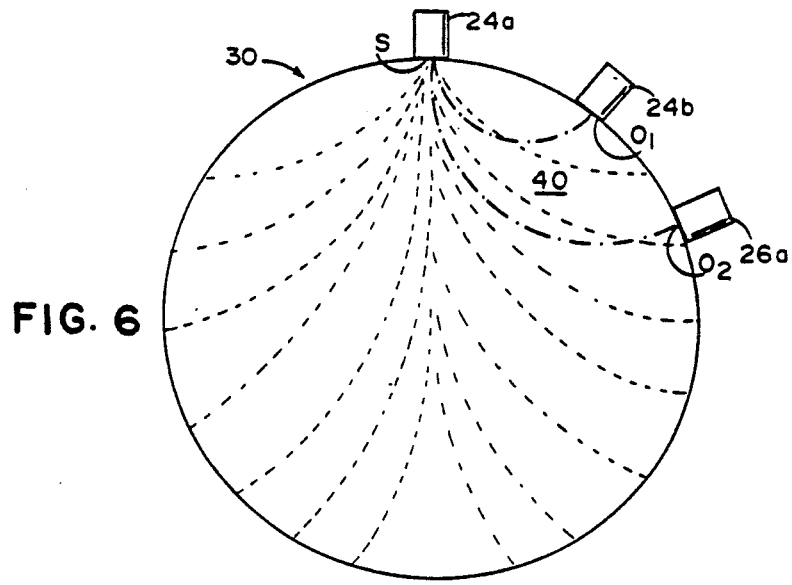
FIG. 6 is a second pictorial, schematic illustration showing a second arrangement of light source and light-detection receivers helpful in understanding the present invention.

As disclosed in co-pending application Ser. No. 827,526, referred to above, an internal transducer such as a potentiometer may be utilized to automatically provide an output signal which directly measures the mutual separation of the two component members 24' and 26'. In the same manner, such a transducer may be utilized to automatically indicate the relative changes in position brought about by use of the manually-manipulatable joints 32, 34 and the couplings 36, 38. Accordingly, the component members 24' and 26' of the probe 10' shown in FIG. 2 may be utilized by manipulating the two component members so as to fit any given geometry in the test subject, and thereby to sample a particular selected internal volume thereof, generally as illustrated in FIGS. 5 and 6, and in so doing the aforementioned transducers will provide outputs automatically determinative of the particular spacial positioning of the two probes relative one another. The three degrees of relative movement described above are generally sufficient to conform to most in vivo test subjects; of course, a further such degree of freedom could be provided by a rotary coupling disposed in a plane generally orthogonal to that of the supports for the component members 24' and 26', such that the two may be disposed along axes positioned at an acute angle with respect to one another.

Figure 3:
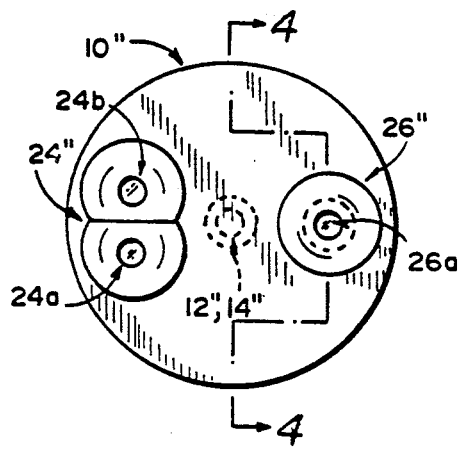
FIG. 3 is an end view of another example of an optical probe useful in practicing the present invention.
Figure 4:
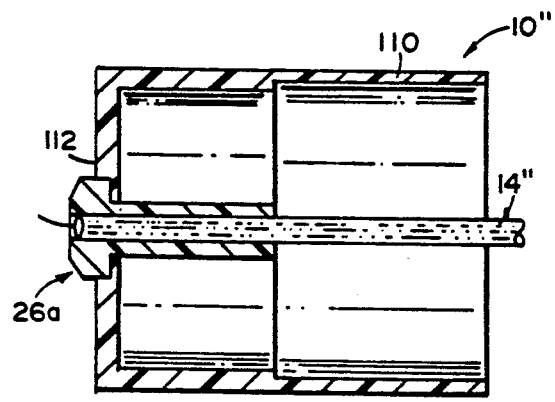
FIG. 4 is a side elevational view of the probe shown in FIG. 3.

The probe 10" illustrated in FIGS. 3 and 4 is a further example of a somewhat simplified version of an instrument generally characterizing the foregoing discussion but having the positions of the source and both the near and far receivers fixed in a predetermined relative location (in this regard, it is to be noted that the particular position of the source with respect to the near receiver may also be changed, and varied, generally in accordance with the variable probes discussed above). Thus, as illustrated in FIGS. 3 and 4, the probe 10" includes a source 24a, a near receiver 24b, and a far receiver 26a, all of which are mounted in the same support structure (here, a cylindrical housing 110 having an end wall 112) at relative positions which are particularly selected to sample a specific and predetermined tissue volume within a particular test subject, for example comparable to that depicted in FIG. 6 (i.e., the arcuately-sided somewhat cone-like volume whose transverse section is designated by the numeral 40 in FIG. 6). In this arrangement, the source 24a and near receiver 24b may be considered the "first component member" 24" and the far receiver 26b considered the "second component member," i.e., the first and second component members constituting opposite halves of the probe 10".

In point of fact, a probe 10" such as that illustrated in FIGS. 3 and 4 may be specifically designed with the relative locations of the source 24a, the near receiver 24b, and the far receiver 26a, all selected so that the configuration samples a very particular physiological area or volume, in which particular physiologic structure exists, for example, a particular volume within the head located beneath the scalp and skull, which may be selected to include only a small number of brain gyra. At the same time, the location of the "near" receiver may be chosen so that it primarily samples only the skin and selected adjacent matter (e.g., in a probe configured for the head, only or primarily the scalp and skull), so that these effects may be removed from the resulting data when the "near" detector output is subtracted from the "far" detector output. In such a probe designed for the top portion of the human head (which has very little musculature) the elements are located as indicated in FIG. 3 and separated by a distance of about eight mm. between the source 24a and the near receiver 24b, and a distance of about twenty-five mm. between the common transverse axis of the source 24a and near receiver 24b, on the one hand, and the far receiver 26a on the other. For simplicity, the source 24a and receivers 24b, 26a are shown in this FIG. as simply being a fiber optic 14" terminating flush with a polymeric support grommet 48, the source fiber optic leading back to a light source and the receiver fiber optics leading back to electro-optical detectors. Other configurations are shown in the above-identified, referenced and incorporated applications.

Figure 7:
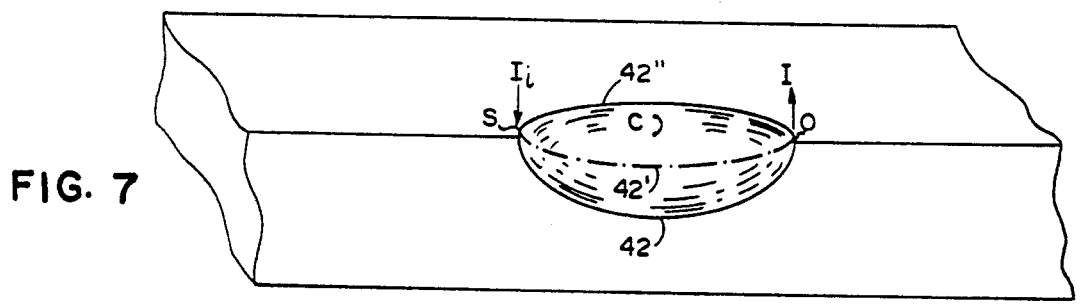
FIG. 7 is a pictorial, schematic illustration somewhat similar to FIGS. 5 and 6 but showing further aspects of optical probe geometry in accordance with the present invention.

The sketches shown in FIGS. 5 and 6 constitute simplified illustrations of the mean distribution of optical paths (referred to hereinafter as the mean optical path) for light travelling from source point S to a receiver point 0 (designating output) in a medium having much higher scattering characteristics than absorption, such as is essentially the case in the in vivo tissue examination constituting the subject matter of Applicants' prior and present patent applications. In such a case, the shape of the mean optical path is spherical (or in any event partially spherical) (which is intended to be illustrated in all of FIGS. 5, 6, 7, 8 and 9). In FIG. 7, this spherical mean optical path is designated by the curved loci 42, 42′, and 42″, which have a center C located at the mid-point of a line extending through points S and 0. In the idealized case illustrated in FIG. 7, where light enters and leaves through a planar surface of a homogenous medium of the type referred to, the sampled volume between points S and 0 is thus hemispherical.

The spectral attenuation of light under conditions such as those referred to above, and shown pictorially in FIG. 7, is affected by the absorption characteristics of the media being transmissed and the optical path length. The absorption characteristics are thus a function of the particular absorptivities ($\alpha$) of specific molecular bonds, multiplied by the concentrations ($\gamma$) of these molecules. The attenuation due to absorption by a specific molecular bond in such a medium is thus described as:

$$\frac{I}{I_1} = e^{-\alpha \gamma l}$$

where:
I = output intensity
$I_1$ = input intensity
$\alpha$ = absorptivity of the molecular bond
$\gamma$ = concentration of the molecular bond in the optical field
l — optical path length The primary underlying principle of optical absorption spectroscopy such as that referred to herein and in the referenced and incorporated prior patent and applications may be considered to be the proposition that relative concentrations of molecular bonds may be determined from the known or determined quantities referred to in the preceding paragraph, in which the quantity (l is related to the aforementioned mean path length by the expression:

$$l = C_{sc} \cdot l^1$$

in which:
$l^1$ = length of the mean path
$C_{sc}$ = scatter factor, from multiple scattering events As indicated above, in many applications or instances the examining light spectra must not only travel through a particular boundary material or structure (such as skin, bone, etc.) which is different than the particular tissue or substance composition within the organ or body part desired to be examined, but in addition there may be a particular area further within such organ or body part whose particular attributes are to be examined, and it is desirable to do so without having the data influenced by the characteristics of adjacent generally similar tissue (e.g., as generally illustrated in FIG. 6). Such a situation is more particularly illustrated in FIG. 8, which generally depicts a model for light travelling through two distinguishable media, or in any event media locations, designated 44 and 46, respectively, volume one constituting in effect a layer of thickness "t." Thus, in FIG. 8 the examining light spectra originally originated at source S, with an intensity $I_i$, passes through layer 44, and then transmisses tissue volume 46 along a mean path 42′, which may be considered semicircular in shape, from a virtual source S′ to a virtual output point O′, from where it passes directly back outward through layer 44 to an actual output point O.

Figure 8:
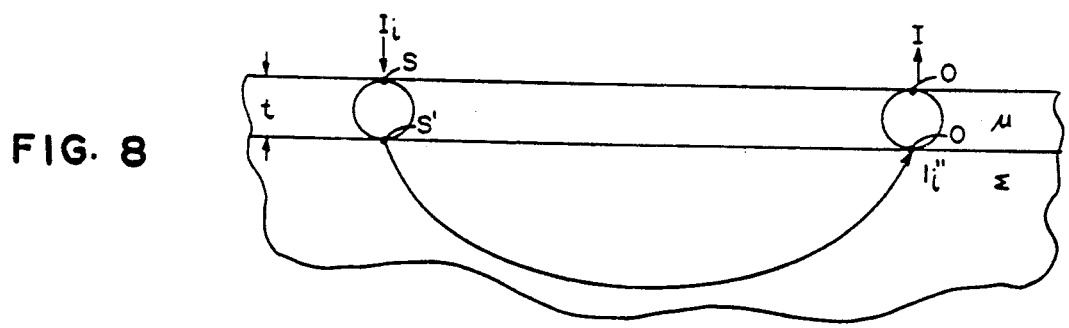
FIG. 8 is a further view similar to that of FIG. 7 but showing other aspects of probe geometry.

With further reference to FIG. 8, the length of the mean optical path 42′ is given by the expression:

$$l_\mu = \pi \cdot C_{sc\mu} \cdot t$$

in which the layer or region 44 comprises a medium having characteristics described or determined by the factor "$\mu$."

Considering that area 46 comprises a different medium having characteristics "$\epsilon$," the light passing through virtual source S′ traverses a path whose length is characterized by mean path 42″, which path length is given by the expression:

$$l_{68} = \pi \cdot C_{sc\epsilon} \cdot [O' - S']$$

Of course, the incident light must also pass back out through layer 44 in order to be detected at point O (as intensity $I_o$). Thus, a further calculation, or repetition, of the expression set forth above for calculating 1 is required.

Accordingly, the overall attenuation of the incident light $I_i$ in traversing layers 44 and 46 and ultimately being detected at point O, as intensity $I_o$, may be determined as follows:

$$\frac{I_i'}{I_i} = e^{-\alpha\gamma\mu l\mu} = e^{-\alpha\gamma\mu\pi C_{sc\mu}t}$$

$$\frac{I_i''}{I_i'} = e^{-\alpha\gamma\epsilon l\epsilon} = e^{-\alpha\gamma\epsilon\pi[S-O]C_{sc\epsilon}}$$

$$\frac{I_o}{I_i''} = e^{-\alpha\gamma\mu\pi C_{sc\mu}t}$$

$$\frac{I_o}{I_i} = \frac{I_i'}{I_i} \cdot \frac{I_i''}{I_i'} \cdot \frac{I_o}{I_i''} = e^{-\alpha\pi\gamma\epsilon[S-O]C_{sc\epsilon}} \cdot e^{-2\alpha\pi C_{sc\mu}t}$$

Figure 9:
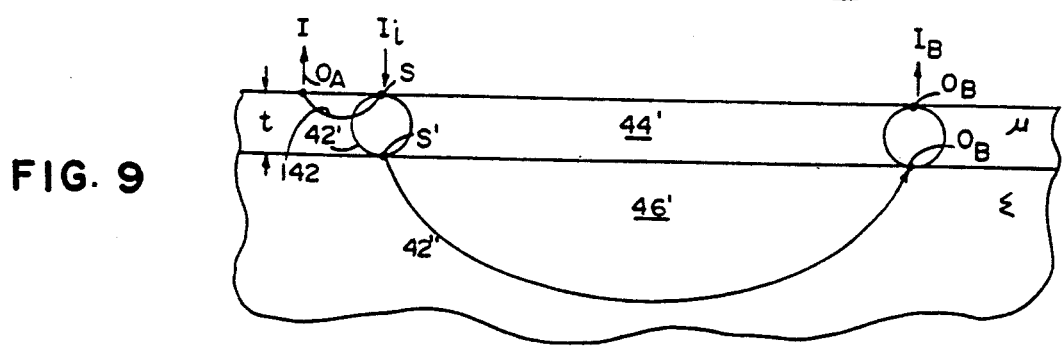
FIG. 9 is a further view similar to that of FIGS. 7 and 8, but showing further aspects of probe geometry.

Accordingly, in a two-sensor system of the type illustrated generally in FIG. 6, the relationship is that indicated in FIG. 9, in which the actual and virtual sources S, S' are depicted in the manner discussed in connection with FIG. 8, but in which a first "near" receiver is disposed at a first output point $O_a$, at which a light intensity $I_a$ is detected, and a second (far) receiver is located at an output point $O_b$, where a light intensity $I_b$ is detected. In accordance with the discussion set forth above, it will be appreciated that by use of such a system the effects of light transmittal through medium "$\mu$" may be removed from the resulting optical response data actually used to assess the state or condition of the internal tissue volume desired to be examined.

That is, as stated above, the separation between the source S and the location of the "near" receiver ($O_A$ in FIG. 9) may be used to control the depth of the mean optical path therebetween (designated 142 in FIG. 9), which may thus be made to correspond to mean path 42', extending between actual source S and virtual source S'. Of course, mean path 42' actually does traverse the entire thickness of medium 44' (of characteristics $\mu$), while mean path 142 is of the same path length but extends laterally through layer 44' rather than transversely across it. Accordingly, the output at $O_A$, comprising intensity $I_A$, will characterize the layer 44' (which, in the case of cranial examination, will characterize the scalp and skull). As already indicated, by use of the subtractive processing in accordance with the invention, the resulting data will characterize only the tissue transmissed along mean path 42'', i.e., will be devoted exclusively to revealing the characteristics of medium $\gamma$.

That is, with reference to the equations set forth previously, and assuming that the dimension "t" is known (actually determined empirically or approximated in accordance with known information), and assuming further that the scatter factors $C_{sc\mu}$ and $C_{sc\gamma}$ are approximately equal (designate $C_{sc}$ below for convenience), the light intensity ratio characteristic of mean path 42'' (the "deep" tissue), plus that attributable to mean path 42' extending through layer 44', is given by the expression:

$$\frac{I_B}{I_i} = e^{-\alpha\pi\gamma\epsilon[S-O_B]C_{sc} - 2\alpha\pi\gamma\mu t C_{sc}}$$

The analogous intensity ratio relative to only the layer 44' (the "shallow" mean path) is given by the expression:

$$\frac{I_A}{I_i} = e^{-\alpha\pi\gamma\mu[S-O_A]C_{sc}}$$

By converting to logarithmic form for convenience, the subtraction of the second expression just set forth above from the first such expression is readily accomplished; therefore, the light intensity data characteristic of only mean path 42'' (i.e., the "deep" data which characterizes only medium 46', of characteristics "$\epsilon$") is given by the expression:

$$-\alpha\pi\gamma\epsilon[S-O_B]C_{sc} = \left(\ln\frac{I_B}{I_i}\right) - \frac{t}{[S-O_A]} \cdot \left(\ln\frac{I_A}{I_i}\right)$$

Accordingly, it will be seen that by careful selection of the relative positions of the "near" and "far" receivers, in relation to the source, and by practice of the subtractive data conditioning contemplated by the present invention, selected internal tissue volumes may be examined on a non-invasive basis without "contamination" by the characteristics of other adjacent tissue or body structure.

The quantified and conditioned data provided through the practice of the present invention, may advantageously be displayed in a number of ways, e.g., by tables of magnitudes and by various forms of plots and graphical presentations utilizing the compensated and weighted magnitudes, whether specifically portrayed in relation to wavelengths or otherwise, not only by means of separate graphical presentations for each different location from which data is obtained, but also by taking complementary scans of complementary body portions. For example, in the case of breast examination, by taking a set of measurements for both breasts with similar relative positioning of the hand instrument 10, i.e., both left and right breasts along the inner (central) marginal edges, along the outer marginal edges, centrally near the chest wall, and centrally outward away from the chest wall. The resulting data provided in accordance with the invention may also be presented in the form of color maps, by use of known color-mapping programs commercially available for digital computers of the type referred to herein. For example, the data obtained for particular wavelength groupings may be assigned different colors, and the colors overprinted within a map area as a function of received signal intensity after conditioning as described hereinabove. This will yield yet another form of data presentation which will have widely-differing color content and distribution, according to the characteristics of the tissue sampled, which will have different evaluative effects for different persons which may be preferred by some. Regardless of which particular form of data presentation is selected, the formatted data may then be meaningfully compared to similarly formatted data for the same patient, and the records so obtained preserved for comparison with similar records taken at other points in time. Further, such results may be comparatively examined with respect to other results obtained from other particular individuals, both those who may be known to be "normal" (i.e., not known at that time to possess specific and identified abnormality or disease), as well as for those who may have diagnosed abnormality or illness.

It is believed self-evident that consideration of the results obtained in accordance herewith and as discussed in the related and referenced applications and patent identified above demonstrates not only the presence of meaningful data but also the potential of a highly useful methodology. In this respect it is not the purpose of this specification to assert a complete, comprehensive and finalized description and explanation of all of the very complex physical and chemical factors involved in the propagation of light through living tissue, nor for every meaningful aspect of the data obtained by the method and apparatus disclosed; further, it is not intended to teach complete and definitive methodology for specific medical diagnosis. Instead, it is intended to show highly useful methods and apparatus for clinical examination and study of human subjects, and for presentation of the data so achieved, including comparative presentations for similar positions on different but analogous body portions of the same patient, and for a broad cross section of different patients at both the same and different ages, and also with respect to particular patients at various different points in their lifespan. Thus, while the invention contemplates the presence of clinically efficacious modalities which may be useful for many purposes perhaps including diagnosis of particular conditions and/or illness, it is presently contemplated that perhaps the most useful contribution of the invention is to provide a screening device and modality in which a familiar and therefore non-frightening medium (i.e., "light") is utilized in a harmless and non-invasive procedure made possible by relatively inexpensive apparatus operable by medical technicians as opposed to physicians themselves, primarily useful for indicating the need (or lack thereof) for much more intensive analytical investigation, i.e., mammography, ultrasound, biopsy, etc.

It should be noted that the instant application and the related and referenced cases disclose concepts and methodologies principally described as applicable to study of the human female breast, but which are not at all limited to use for this purpose That is, optical response and particularly spectral response data obtained in the manner described herein is definitely considered to be appropriate for, and valuable in, examination of other body portions, human or otherwise. While it may or may not be true that a given such application may call for slightly varying the specifics of the modality in actual application, the basic underlying concepts should nonetheless prove applicable and effective. Accordingly, the scope of this patent should be determined by consideration of the appended claims rather than with respect to specific attributes or parameters set forth above and/or in the attached drawings, describing and illustrating various preferred embodiments or characteristics, the scope of the claims to be determined through appropriate application of established principles of patent law including the doctrine of equivalents.

The embodiments of the invention in which an exclusive property or privilege is claimed are defined as follows:

1. A method of non-obtrusively and non-invasively examining the conditional state of physiological substance located within a particular internal volume inside a test subject by optical response, comprising the steps: introducing light of selected wavelengths into said subject from a source location on the outside periphery of said subject; selecting at least first and second light-detection locations on said subject at points spaced from one another and spaced from said source by unequal first and second distances such that a first mean optical path is established extending through a portion of said subject disposed between said source and said first detection location and a second mean optical path of a different length is established extending through a different portion of said subject disposed between the source and said second detection location, said second optical path extending through said particular internal volume while said first optical path generally lies within a different internal volume located nearer said source location than and said particular internal volume; detecting the intensity of light of said selected wavelengths at said first and second detection locations resulting from said introduction of light at said source location; and differentially comparing the said light intensities detected at said first and second detection locations to thereby obtain examination data which particularly characterizes said particular internal volume without effects attributable to said different internal volume.

2. The method of claim 1, wherein said step of differentially comparing comprises subtraction of optical response data obtained by detecting said light intensity at said second location from optical response data obtained by detecting said intensity at said first location.

3. The method of claim 1, wherein said physiological substance comprises a highly scattering and partially absorptive media and said light wavelengths, source location and detection locations are selected such that said mean optical paths comprise generally spherical curves.

4. The method of claim 3, wherein said step of differentially comparing comprises subtraction of optical response data obtained by detecting said light intensity at said second location from optical response data obtained by detecting said intensity at said first location.

5. The method of claim 1, including the step of selecting a test subject which comprises a body extremity having internal tissue of a nature different than its external periphery, and wherein said light is selected and introduced in a manner such that said second optical path traverses said internal tissue at a depth well beyond said external periphery while said first optical path length lies primarily within said external periphery.

6. The method of claim 5, wherein said step of differentially comparing comprises subtraction of optical response data obtained by detecting said light intensity at said second location from optical response data obtained by detecting said intensity at said first location.

7. The method of claim 1, wherein said test subject comprises the head of an animate being and said light is introduced and detected such that said second path is sufficiently long to traverse the brain tissue while said first path is sufficiently short to traverse primarily only the scalp and skull.

8. The method of claim 7, wherein said step of differentially comparing comprises subtraction of optical response data obtained by detecting said light intensity at said second location from optical response data obtained by detecting said intensity at said first location.

9. The method of claim 7, wherein said light is introduced and detected in a manner such that said second optical path is selected to have a length which traverses a predetermined internal brain area.

10. A method of appraising the internal structure of selected organic bodies and materials wherein light energy is used as an investigative media by transmitting it through said bodies and materials and producing quantitative data from such light which characterizes the composition, condition and/or physiology of a particular area of said internal structure, comprising the steps of:

placing optical source and receiver probe members in optically-coupled relation with the selected body or material and sending light of selected wavelengths from said source probe member into the selected body or material to transmiss the same;

receiving the resulting light from said body or material at separate and mutually-spaced first and second locations, said first location being near that at which said selected light is sent into said body or material from said source in relation to said second position;

quantifying the resulting light which is received at said first location as well as quantifying the resulting light received at said second location to obtain optical response data values; and using said data values for resulting light received at said first location to condition the said data values for resulting light received at said second location by modifying one such set of quantified data values as a function of the other, to thereby remove from the resulting conditioned light-response data values optical effects resulting from factors attributable to impingement of the light upon and passage thereof through the outer perimeter of the selected body or material, whereby quantified optical response data valuations are obtained which characterize the internal structure of a particular area within said body or material on a generally intrinsic basis and which are substantially independent of perimetral characteristics.

11. A method of quantitatively characterizing internal organic structure according to claim 10, in which said different wavelength-related data value representations for said first and second locations are combined by comparatively differencing them.

12. A method of quantitatively characterizing internal organic structure according to claim 11, in which said step of receiving resulting light at a first location disposed relatively near that at which said light is sent into said body or material from said source is carried out by using a detector which is carried with said source and disposed at a measured distance from the location of light emission therefrom.

13. A method of quantitatively characterizing internal organic structure according to any of claims 10, 11 or 12, in which said step of receiving resulting light at said first location includes receiving such light at a point located not more than about five centimeters from the place at which said selected light is introduced into said selected body or material.

14. A method of quantitatively characterizing internal organic structure according to any of claims 10, 11 or 12, which includes the steps of:

establishing a measure of the nominal optical distance between said first and second locations of light reception while said probe members are held in said optically-coupled relation; and conditioning the quantified wavelength-related optical response data values by modifying them in accordance with the particular nominal optical distance between said probe members whose measure has been determined with said probe members fixed in said optically-coupled relation, to thereby produce numeric optical response data which quantitatively characterizes the internal structure of said body or material on a wavelength-related basis which is substantially independent of the distance between said first and second receivers, and which is thus directly comparable with other such quantitative and conditioned data obtained from other and different organic bodies or materials.

15. A method of quantitatively characterizing internal organic structure according to any of claims 10, 11 or 12, which includes the further steps of:

preparing composite averages of said quantified and conditioned wavelength-related data values from a plurality of different individual organic bodies or materials; and using said composite averages as a basis for comparison with the quantified and conditioned data values obtained from a particular individual organic body or material.

16. A method of quantitatively characterizing internal organic structure according to claims 11 or 12, which includes the steps of:

moving said optical probe members from said first and second locations to other pairs of locations on the same such body or material;

holding said optical probe members in optically-coupled relation with such body or material at such other locations; and repeating said steps of sending selected light wavelengths, receiving resulting light, quantifying and conditioning received light data values by modifying the data values for one of the locations in a pair as a function of the data values for the other such location in that pair, to thereby condition the light-reception data for such other locations and thus provide meaningful mutual comparison with other such quantified and conditioned data regardless of the particular location at which it was obtained.

17. A method of quantitatively characterizing internal organic structure according to claim 16, which includes the further steps of preparing composite averages of said quantified and conditioned wavelength-related data values from a plurality of different individual organic bodies or materials, classifying said composite averages as a function of their corresponding investigative wavelength, and using such classified composite averages as a basis for comparison with the particular quantified and conditioned data values obtained from a specific individual organic body or material.

18. Apparatus for obtaining optical response data from organic bodies which is representative of the internal nature of tissue within such bodies, including:

at least one optical probe member including a source and at least two receivers adapted for placement in operational proximity with selected areas on said body and adapted to pass light of selected wavelengths from said source to said receiver through such body;

means for holding said source and receivers in predetermined relation while in their said positions of operational proximity to the selected areas of the said body;

said receivers including means for receiving the resulting light which has passed through said body at a first position with respect to said light source as well as means for receiving such light at a second position located further away from said source than said first position, and for producing corresponding quantified data values for each such position which are correlated with said selected wavelengths; and means for modifying the said quantified data values for light received at one such position as a difference function of the corresponding data values for light received at the other such position in a manner such that the resulting quantified and modified data values are representative of intrinsic interior characteristics of said body and generally free of optical effects resulting from factors attributable to impingement of the light upon and passage thereof through the outer perimeter of said body and in a manner such that said resulting data values are primarily representative of the conditional state of a particular internal tissue volume whose location within said body is predetermined by the particular location and disposition of said first and second positions relative one another;

said first light-receiving means carried with said optical probe member at a position within not more than about ten centimeters from the location of said light source, for receiving certain of said light projected by said source into said body following scatter effects upon said light occurring within said body at a location relatively close to said source, and said second receiving means being positioned further from said light source and within about thirty centimeters from the location of said light source.

19. Optical response apparatus according to claim 21, wherein said first receiving means is carried with said optical probe member at a position closely adjacent said light source.

20. Apparatus according to claim 18, wherein said light source and at least a first one of said receivers is carried by a common optical probe member.

21. Apparatus according to claim 20, wherein said common probe member further carries a second optical receiver.

22. Apparatus according to claim 21, wherein said probe member comprises a single probe unit in which said source and said first and second receivers are mounted.

23. Apparatus according to claim 22, wherein said first and second receivers are mounted in said probe member in fixed position.

* * * * *

UNITED STATES PATENT AND TRADEMARK OFFICE
CERTIFICATE OF CORRECTION

PATENT NO. : 5,139,025

DATED : August 18, 1992

INVENTOR(S) : Gary D. Lewis, Hugh F. Stoddart

It is certified that error appears in the above-identified patent and that said Letters Patent is hereby corrected as shown below:

Column 9, line 8
    "accomplished y" should be -- accomplished by --.

Column 10, line 11
    Before "receivers" delete -- 1. --.

Column 12, lines 18 & 19
    "quantity (" should be -- quantity $\ell$ --.

Column 12, line 11
    "1 - optical" should be -- $\ell =$ optical --.

Column 12, line 22
    "1 = $C_{sc}$ $1^1$" should be -- $\ell = C_{sc} \ell^1$ --.

Column 12, line 24
    "$1^1=$" should be -- $\ell^1=$ --.

Column 12, line 54
    "$1_\mu=$" should be -- $\ell_\mu=$ --.

Column 12, line 63
    "$1_{68} = \pi \cdot C_{sc\varepsilon}$" should be -- $\ell_\varepsilon = \pi \cdot C_{sc_\varepsilon}$ --.

Column 13, line 1
    "calculating 1" should be -- calculating $\ell$ --.

Column 13, line 33
    After "examined" insert -- . --.

Column 13, line 53
    "medium $\gamma$" should be -- medium $\varepsilon$ --.

Column 15, line 43
    After "purpose" insert -- . --.

UNITED STATES PATENT AND TRADEMARK OFFICE
CERTIFICATE OF CORRECTION

PATENT NO. : 5,139,025
DATED : August 18, 1992
INVENTOR(S) : Gary D. Lewis, Hugh F. Stoddart It is certified that error appears in the above-indentified patent and that said Letters Patent is hereby corrected as shown below:

Column 16, line 47
    Before "lies" delete --length--.

Column 16, line 57
    After "traverse" delete --the--.

Signed and Sealed this

Twenty-eighth Day of December, 1993

Attest:

BRUCE LEHMAN

Attesting Officer

Commissioner of Patents and Trademarks